(12) United States Patent
Hatfield et al.

(10) Patent No.: US 7,694,578 B2
(45) Date of Patent: Apr. 13, 2010

(54) METHOD OF EVALUATING MATERIALS USING CURVATURE

(75) Inventors: David B. Hatfield, Oracle, AZ (US);
Terry M. Sanderson, Tucson, AZ (US);
Renee M. Rodgers, Sahuarita, AZ (US)

(73) Assignee: Raytheon Company, Waltham, MA (US)

( * ) Notice: Subject to any disclaimer, the term of this patent is extended or adjusted under 35 U.S.C. 154(b) by 196 days.

(21) Appl. No.: 11/936,247

(22) Filed: Nov. 7, 2007

(65) Prior Publication Data
US 2009/0114032 A1   May 7, 2009

(51) Int. Cl.
*G01D 1/16* (2006.01)
(52) U.S. Cl. .......................................... 73/789; 73/760
(58) Field of Classification Search ............ 73/760–789
See application file for complete search history.

(56) References Cited

U.S. PATENT DOCUMENTS

| | | | | | |
|---|---|---|---|---|---|
| 5,040,154 | A | * | 8/1991 | Mikheev et al. ................ | 367/13 |
| 6,389,906 | B2 | * | 5/2002 | Buck ............................. | 73/849 |
| 6,460,012 | B1 | * | 10/2002 | Welch et al. ................. | 702/182 |
| 6,513,389 | B2 | * | 2/2003 | Suresh et al. .................. | 73/785 |

OTHER PUBLICATIONS

Stein, NiCoForm, Inc., A Practical Guide to Understanding, Measuring and Controlling Stress in Electroformed Metals, http://www.finishing.com/Library/stein/strspapr.html; 6 pages, Aug. 17, 2006.
Stein, NiCoForm, Inc., Fast and Accurate Deposit Internal Stress Determination, 4 pages, Aug. 17, 2006.

\* cited by examiner

*Primary Examiner*—Max Noori
(74) *Attorney, Agent, or Firm*—Renner, Otto, Boisselle & Sklar, LLP

(57) ABSTRACT

A method of evaluating material properties of polymeric materials includes making one or more material samples or slabs, with each of the samples or slabs having a pair of material layers in contact with one another. The layers are layers of organic matrix polymer material that have different characteristics from each other, for example having a difference in composition and/or cure characteristics. Characteristics of the test slabs and the interface between the layers can be determined by examining curvatures of the test slabs. A number of samples may be made up having the same material in a first layer, and range of different materials in the respective second layers. The range may cover a range of various material compositions and/or cure characteristics.

20 Claims, 2 Drawing Sheets

METHOD OF EVALUATING MATERIALS USING CURVATURE

BACKGROUND OF THE INVENTION

1. Technical Field of the Invention

Invention relates to the field of determination of properties of polymer materials.

2. Description of the Related Art

Prior attempts to identify combinations of specific polymers and polymer additives that would minimize residual stress have most often been done on a trial and error basis. Some attempts have been made in the literature to use ultrasonic techniques to measure residual stress in materials, but ultrasonic techniques are typically expensive, time consuming, and often not sufficiently sensitive to yield accurate measures. Ultrasonic residual stress measurement techniques have not in general evolved beyond academic studies.

From the foregoing it will be appreciated that improvements would be desirable in measurements of residual stresses and in determining the effect of various changes in the materials on these residual stresses.

SUMMARY OF THE INVENTION

According to an aspect of the invention, a method of evaluating material characteristics includes examining curvature of one or more test slabs that each include layers of curable organic matrix material with at least one of different composition or different cure characteristics between the layers. The curvature of different test slabs may be compared to determine the effect of a dependent variable, such as particle load or cure time and/or temperature, on material characteristics. Alternatively, the curvature may be used to determine residual stress at an interface between the layers, when the material properties one of the layers is known.

According to another aspect of the invention, a method of evaluating material properties includes the steps of: forming a test slab of organic matrix material, wherein the test slab includes a first layer of curable organic matrix material in contact with a second layer of curable organic matrix material, and wherein the layers have at least one of different composition or different cure characteristics; examining curvature of the test slab; and determining a material characteristic of the organic matrix material from the curvature of the test slab.

According to yet another aspect of the invention, a method of evaluating material properties includes the steps of: forming plural test slabs of organic matrix material, wherein the test slabs includes first layers of curable organic matrix material in contact with respective second layers of curable organic matrix material, wherein the layers each of the test slabs have at least one of different composition or different cure characteristics, and wherein the first layers of the test slabs have at least one of different composition or different cure characteristics from each other; and comparing curvatures of the test slabs to determine material characteristics of the test slabs.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

In the annexed drawings, which are not necessarily to scale.

DETAILED DESCRIPTION

A method of evaluating material properties of polymeric materials includes making one or more material samples or slabs, with each of the samples or slabs having a pair of material layers in contact with one another. The layers are layers of organic matrix polymer material that have different characteristics from each other, for example having a difference in composition and/or cure characteristics. Characteristics of the test slabs and the interface between the layers can be determined by measuring or otherwise examining the curvature of the test slabs. A number of samples may be made up having the same material in a first layer, and range of different materials in the respective second layers. The range may cover a range of various material compositions and/or cure characteristics. For example, a range of particle loading, mix ratios, or cure times and/or temperatures may be covered. The method provides a quick and relatively inexpensive way of determining the overall effect on material properties of a wide range of characteristics. The method of testing samples over a wide range of composition and/or cure characteristics may be used as a first step to find a narrower range of composition and/or cure characteristics for more intensive and more precise (but more time consuming and/or more expensive) subsequent testing.

Figure 1:
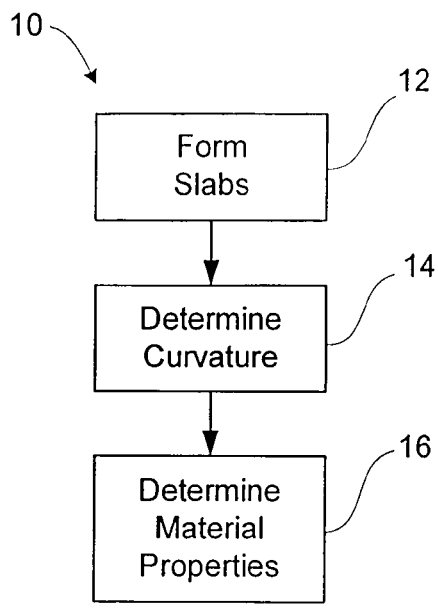
FIG. 1 is a high-level flow chart showing steps of a method in accordance with an embodiment of the present invention.

FIG. 1 shows several high-level steps of method 10 for evaluating materials and determining material properties. In step 12 of the method 10 one or more specimens or slabs are formed. As explained in greater detail below, the slabs include a pair of material layers that have different material properties, and which are in contact with one another. In step 14 the curvature of the one or more test slabs is determined. This determination may involve actual measurement of the curvature, or may involve other evaluations of curvature, such as comparing curvature of different test specimens or slabs. Finally, in step 16, the curvature is used to determine material properties. The determination of material properties is intended to broadly cover a wide range of possible uses of the curvature information to determine one or more characteristics of the materials of the test specimens or slabs. Determining material properties is broader than merely assigning a numerical value to some property of some material, although determining material properties may include such an operation.

Figure 2:
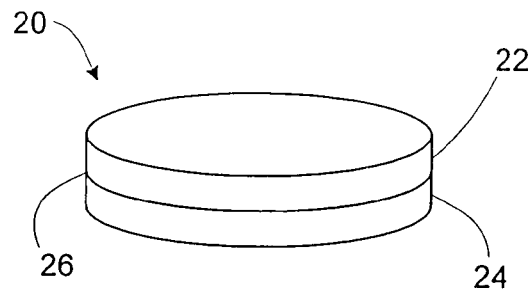
FIG. 2 is an oblique view of a test sample or slab used in the method of FIG. 1.

FIG. 2 shows an example of a test specimen or slab 20. The slab 20 has a pair of material layers 22 and 24 that are in contact with one another along an interface 26. The layers 22 and 24 are made of curable organic matrix polymer materials.

The material in the first layer 22 has different characteristics from the material in the second layer 24. This leads to residual stresses along the interface 26. The difference in the materials between the layers 22 and 24 may be differences in composition and/or cure characteristics. Differences in composition may include different loading of the two materials by particles such as nanoparticles. Loading is the weight percentage of a material that is made up of inserted particles. It will be appreciated that changes in loading can affect characteristics of the resulting material. In addition, loading with different particle types may affect characteristics.

Another possible composition difference between the respective materials of the two layers 22 and 24 is a difference in mix ratio. Organic matrix polymer materials are made by combining two or more component materials, such as an epoxy resin, a curing agent, and a filler (fibers). More broadly, other resins may be used in the material. It will be appreciated that changing the ratio between the component materials can affect the material properties of the resulting mixed and cured polymer material.

Material properties may also differ due to differing cure characteristics of the material in the layers 22 and 24. Final material properties of a polymer matrix material may depend on the time and temperature of the cure process used to allow the material to crosslink or harden after the mixing of the components. Different cure characteristics produce materials with different polymer chain characteristics, such as in terms of length of the polymer chains and cross linking of the polymer chains. These differences may result in different material properties. Another difference in material properties may be in providing different orientations for oriented fillers (fibers).

The slab 20 may have any of a wide variety of sizes and shapes. As shown in FIG. 2, the slab 20 may have a disc shape, with a thickness much less than its diameter. Alternatively the slab may have a rectangular shape, or any other shape so long as the specimen dimensions are much larger (at least a factor of ten) than the overall specimen thickness. Since having the test slab or specimen 20 curve is necessary for the method 10 to be carried out, it is advantageous for a test specimen or slab 20 to have a configuration such that residual stresses at the interface 26 can result in measurable or readily observable curvature.

The test slab or specimen 20 may be produced using a mold having an appropriately-shaped cavity. The mold may be a flat mold. The material of the first layer 22 is formed (mixed and cured) within the mold cavity, and then the second layer 24 is formed in contact with the first layer 22.

Figure 3:
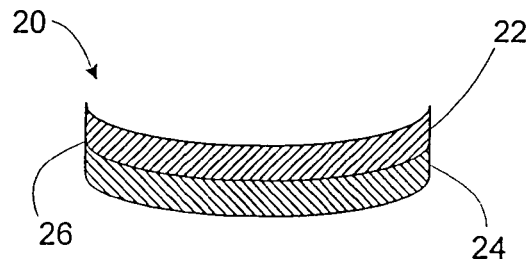
FIG. 3 is a cross-sectional view illustrating curvature of the test slab of FIG. 2, due to residual stresses.

When the slab 20 is removed from the mold, residual stresses at the interface 26 can result in curvature of the slab 20, as illustrated in FIG. 3. The amount of curvature of the slab 20 depends upon the dimensions of the slab 20. A typical deflection value is 20-30 thousandths of an inch (0.50-0.76 mm). For situations, in which the mechanical behavior of the specimen is linear, the specimen radius of curvature is expected to be substantially the same at all parts of the slab 20. In such cases the slab 20 assumes a parabolic deflection curve with a uniform radius of curvature.

In situations where there is a nonlinear change in material properties, the slab 20 may assume a different shape. The radius of curvature in such a condition is expected to be non-uniform and dependent upon the shape of the slab 20. Slabs in this nonlinear response region can obtain more complicated shapes, for example having a saddle shape resembling a potato chip.

A wide variety of methods are possible for measuring curvature of the test slab 20. As used herein, measuring "curvature" also includes measurements of deflection of a material. Mechanical methods, such as a coordinate measuring machine, a ruler, or a dial indicator may be used. Laser light or a laser profilometer may also be used to determine deflection of the test slab or specimen 20. Optical methods also may be utilized, for example by providing the slab 20 with a reflective surface and measuring deflection using reflected light.

Curvature measurements for a number of test slabs 20 may be compared to determine the point at which some independent variable has an effect on the overall material properties. For example a series of five slabs may be formed with different loading levels of nanoparticles, for example 1%, 2%, 3%, 4%, and 5% loading. A wide variety of number of samples may be utilized in a single test. It will be appreciated that a great number of samples may be made up and examined relatively rapidly. For situations where loading has no appreciable effect on the material properties, the curvature of the samples with loading will be the similar to that for a no-loading condition. Comparison of the curvature for the different samples may be used to find the point at which loading begins to appreciably affect material properties. This provides an easy way for obtaining a rough idea of the area of most interest in determining when loading begins to have an effect. It will be understood that a similar technique may be used with regard to determining the effect of other dependent variables, such as mixed ratio between components, cure temperatures, and cure times.

Rough comparisons between samples may be made even without measuring curvature of the samples. For example, multiple samples may be placed on an overhead projector or optical comparator to compare by sight their overall cross sectional shapes. Changes in curvature that indicate changes in material properties (changes in the residual stress at the interface 26) may be large enough to be detectable with the naked eye.

When forming multiple samples for measuring the effect of a dependent variable or variables on residual stress, it is advantageous to maintain the same dimensions for the slabs. Thus the multiple slabs 20 may have the same shape, the same layer thicknesses, and the same diameter or relevant length dimension. However it will be appreciated that the curvature is not generally dependent upon the size or shape of the slabs, especially 1) when the slabs 20 have material properties that vary linearly with the dependent variable, and 2) when the stiffness of the slabs is not such that curvature due to residual stresses is mechanically restrained to a different degree and different samples. Although analysis of results may be simpler in cases where only one dependent variable is varied over a range of samples, it is possible to vary two or more dependent variables over a range of samples. Also, it is useful for one of the layers in each of the samples to be a control layer that is substantially identical to the corresponding control layers in the other samples. But even this is not an absolute requirement.

The method 10 may also be used to determine residual stress in multi-layered specimens when the material properties of the other layers 22 and 24 are already known. Mathematically, in general material properties cannot be determined, but residual stresses induced can be determined when two dissimilar polymeric materials are used to create an interface.

Figure 4:
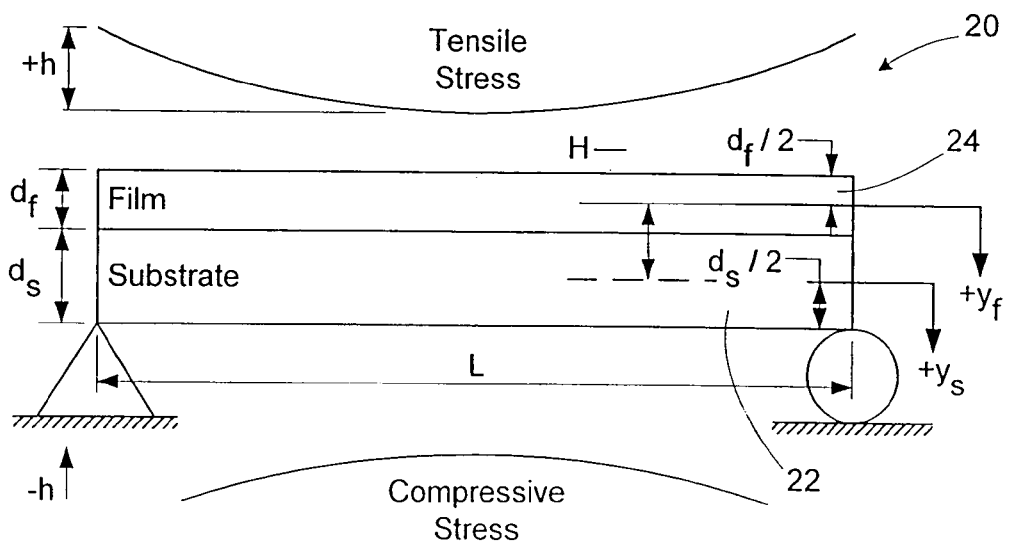
FIG. 4 is an illustration used to describe a method of determining residual stress in accordance with an embodiment of the invention.

With reference to FIG. 4, a method for determining residual stresses is now described. FIG. 4 shows a side view of a bi-layered material specimen that defines the problem geometry. The "substrate" in FIG. 4 is the first layer of polymeric material 22 that is formed. It is taken to be free of residual stress, while the "film" is the second layer 24 of polymeric material, which is cast and/or cured onto the surface of the substrate. Residual stress will form in the film layer 24. If the specimen 20 is entirely free of thermal stress, then tensile and compressive residual stresses in the film will cause the deflections to be as shown in FIG. 4. The linear relations governing the deflections and stresses of a bi-layered beam under these conditions have been derived to show that:

$$\frac{1}{R} = \frac{6d_s^2\beta(1+\beta)[E_f(\alpha_s\overline{T}_s - \alpha_f\overline{T}_f) + \overline{\sigma_R}] + 12M(1+\gamma\beta)}{d_s^3 E_s[3\gamma\beta(1+\beta)^2 + (1+\gamma\beta)(1+\gamma\beta^3)]}$$

$$y = \frac{(L^2 - 4x^2)[3d_s^2\beta(1+\beta)\{E_f(\alpha_s\overline{T}_s - \alpha_f\overline{T}_f) + \overline{\sigma_R}\} + 6M(1+\gamma\beta)]}{2d_s^2 E_s[3\gamma\beta(1+\beta)^2 + (1+\gamma\beta)(1+\gamma\beta^3)]}$$

$$\overline{\sigma_R} = \frac{2hd_s^3 E_s[3\gamma\beta(1+\beta)^2 + (1+\gamma\beta)(1+\gamma\beta^3)] - 6L^2 M(1+\gamma\beta)}{3L^2 d_s^2 \beta(1+\beta)} - E_f(\alpha_s\overline{T}_s - \alpha_f\overline{T}_f)$$

$$\sigma_f = E_f \left\{ \frac{y_f(1+\gamma\beta) - \frac{d_s}{2}(1+\beta)}{(1+\gamma\beta)R} \right\} + \frac{E_f(\alpha_s\overline{T}_s - \alpha_f\overline{T}_f) - \gamma\beta\overline{\sigma_R} + (1+\gamma\beta)\sigma_R}{1+\gamma\beta} \quad -\frac{d_f}{2} \le y_f \le \frac{d_f}{2}$$

$$\sigma_s = E_s \left\{ \frac{y_s(1+\gamma\beta) + \frac{d_s}{2}\gamma\beta(1+\beta)}{(1+\gamma\beta)R} \right\} - \frac{\beta[E_f(\alpha_s\overline{T}_s - \alpha_f\overline{T}_f) - \overline{\sigma_R}]}{1+\gamma\beta} \quad -\frac{d_s}{2} \le y_s \le \frac{d_s}{2}$$

where y is the vertical deflection of the specimen, and where:

$\sigma_f$ = total film stress $\quad$ $\sigma_s$ = total substrate stress
$E_f$ = Young's modulus of film $\quad$ $E_s$ = Young's modulus of substrate
$\alpha_f$ = film $CTE$ (coefficient of thermal expansion) $\quad$ $\alpha_s$ = substrate $CTE$
$R$ = radius of curvature in bending $\quad$ $\sigma_R$ = residual stress in film $$\overline{T}_f = \frac{\int T_f dA_f}{A_f} \quad \overline{T}_s = \frac{\int T_s dA_s}{A_s} \quad \overline{\sigma_R} = \frac{\int \sigma_R dA_f}{A_f}$$

$$M_i = \int \sigma_i y_i dA_i \quad M_R = \int \sigma_R y_f dA_f \quad M_{Ti} = \int T_i y_i dA_i$$

$$\beta = \frac{d_f}{d_s} \quad \gamma = \frac{E_f}{E_s}$$

$$M_R = wM_R' \quad M_{Tf} = wM_{Tf}' \quad M_{Ts} = wM_{Ts}'$$

$$M = \alpha_f E_f M_{Tf}' + \alpha_s E_s M_{Ts}' - M_R'$$

and where the subscripts f and s denote the film and the substrate, respectively.

When the bent strip method is used the specimen is usually isothermal, upon which $T_f = T_s = T$ and the thermal moments vanish. If the residual stress distribution is constant as well then:

$\sigma_R = \overline{\sigma_R}$ and $M_R$ also vanishes, upon which:

$$\overline{\sigma_R} = \frac{2hd_s E_s[3\gamma\beta(1+\beta)^2 + (1+\gamma\beta)(1+\gamma\beta^3)]}{3L^2\beta(1+\beta)} - E_f(\alpha_s - \alpha_f)T$$

These are the final forms of the relations between residual stress and bow out height when using the bent strip method, under isothermal conditions and the assumption of uniform residual stress, as would be typical when applying the ideas contained in the method.

In practice, plate specimens are preferred to beam specimens, although it will be appreciated that various types of specimens may be used. Because both the thermal and residual stresses impose in-plane (x-z) body forces on the specimen, the condition is one of plane stress and all of the equations given above are still valid so long as the Young's modulus E is replaced by the biaxial modulus throughout the above equations, $$E_i \Rightarrow \frac{E_i}{1+v_i}$$

v=Poisson ratio where the subscripts i=f and s. The biaxial stress is the same in both the x and z directions, hence for linear deflections the radius of curvature is also the same in both directions. These relations are thus valid for plates of arbitrary shape, i.e. square, rectangular, circular, etc., so long as the characteristic dimensions of the plate are much greater than the specimen thickness.

If beam specimens are produced, the apparent "residual stress distribution" will not be uniform through the film thickness due to the biaxial effect at the interface, which decays with increasing film thickness. This is a thermoelastic effect that is entirely independent of what the residual stress itself may be, and it can introduce error in the experimental measurement of residual stress. However, if plate specimens are produced then this thermoelastic interference will disappear on the order of one or two specimen thicknesses. Thermoelastic interference can be eliminated from experimental results by using plate specimens, where the plate dimensions are at least ten times the net specimen thickness, and the deflection curve should not be measured (in the x-z plane) any closer than two specimen thicknesses from the edges of the specimen.

Figure 5:
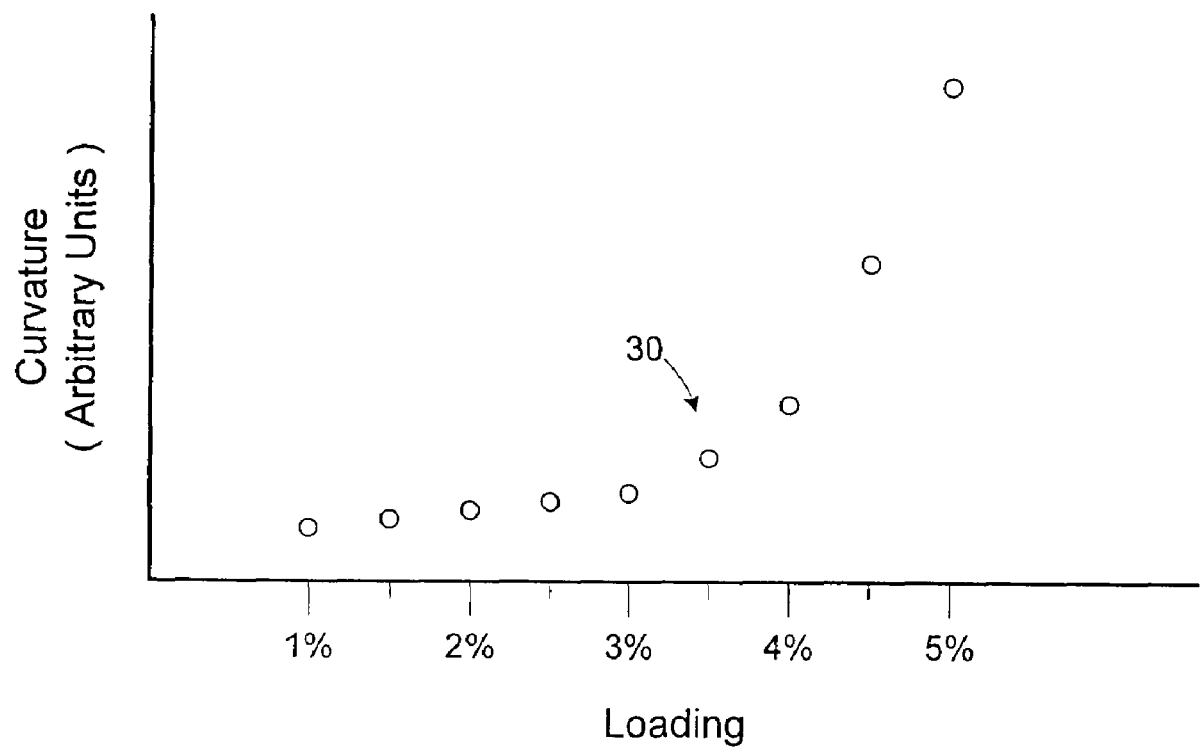
FIG. 5 is a graph qualitatively illustrating possible test results from the method of FIG. 1.

FIG. 5 schematically illustrates test results for a series of six samples with different values of loading. In this example the radical change in curvature from the 3% loading sample to the 4% loading sample, indicated by reference number 30, shows that a rate change in response with respect to particle loading occurs between 3% loading and 4% loading. The samples with varying loading have their loaded layers in contact with similar layers of neat control polymer matrix material (material with no added particles). With the test results shown in FIG. 5, another round of testing could be performed focusing on the 3-4% loading range, to further quantify where the change point between linear and non-linear behavior is. Alternatively other testing methods, perhaps with greater accuracy, could be performed to better quantify the material behavior.

The methods described herein provide a rapid and cost-effective way of obtaining a rough idea of the effect on residual stresses of variations of some dependent variable. By focusing the testing process rapidly on a range of dependent variable areas of interest, much time and testing expense may be avoided. Such methods are useful in characterizing new materials, as well as evaluating possible additives and substitute ingredients.

Another use of the method is in use as a lot-acceptance technique. The method may be used as a rapid and inexpensive check on material properties of a lot of new materials.

A further use of the method is in determining how to deliberately impose a desired residual stress at an interface. This may be done to achieve a desired curvature of a part.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method of evaluating material properties comprises:
    forming a test slab of organic matrix material, wherein the test slab includes a first layer of curable organic matrix material in contact with a second layer of curable organic matrix material, and wherein the layers have at least one of different composition or different cure characteristics;
    examining curvature of the test slab; and
    determining a material characteristic of the organic matrix material from the curvature of the test slab.

2. The method of claim 1, wherein the examining curvature includes measuring the curvature of the slab.

3. A method of evaluating material properties comprises:
    forming a test slab of organic matrix material, wherein the test slab includes a first layer of curable organic matrix material in contact with a second layer of curable organic matrix material, and wherein the layers have at least one of different composition or different cure characteristics;
    examining curvature of the test slab; and
    determining a material characteristic of the organic matrix material from the curvature of the test slab;
    wherein the forming includes forming one or more additional slabs, with each of the additional slabs having a first layers of curable organic matrix material in contact with a second layer of curable organic matrix material, wherein the layers have at least one of different composition or different cure characteristics;
    wherein the first layers of the additional slabs have substantially the same composition and substantially the same cure characteristics as the first layer of the test slab; and
    wherein the second layers of the additional slabs differ from the second slab of the test slab in at least one of composition or cure characteristics.

4. The method of claim 3,
    wherein the forming of the one or more additional slabs includes forming the one or more additional slabs such that the second layers of the additional slabs differ from the second slab of the test slab in composition;
    further comprising examining curvatures of the one or more additional slabs having the second layers that differ from the second slab of the test slab in composition; and
    wherein the determining includes determining the material characteristic of the organic matrix material from both the curvature of the test slab and the curvatures of the one or more additional slabs.

5. The method of claim 4, wherein the forming of the one or more additional slabs includes forming the one or more additional slabs such that the second layers of the additional slabs differ from the second slab of the test slab in loading of particles.

6. The method of claim 5, wherein the forming of the one or more additional slabs includes forming the one or more additional slabs such that the second layers of the additional slabs are spread over a range of loading.

7. The method of claim 4, wherein the forming of the one or more additional slabs includes forming the one or more additional slabs such that the second layers of the additional slabs differ from the second slab of the test slab in mix ratio.

8. The method of claim 7, wherein the forming of the one or more additional slabs includes forming the one or more additional slabs such that the second layers of the additional slabs are spread over a range of mix ratio.

9. The method of claim 3,
    wherein the forming of the one or more additional slabs includes forming the one or more additional slabs such that the second layers of the additional slabs differ from the second slab of the test slab in cure characteristics
    further comprising examining curvatures of the one or more additional slabs having the second layers that differ from the second slab of the test slab in cure characteristics; and
    wherein the determining includes determining the material characteristic of the organic matrix material from both the curvature of the test slab and the curvatures of the one or more additional slabs.

10. The method of claim 9, wherein the forming of the one or more additional slabs includes forming the one or more additional slabs such that the second layers of the additional slabs are spread over a range of cure time.

11. The method of claim 9, wherein the forming of the one or more additional slabs includes forming the one or more additional slabs such that the second layers of the additional slabs are spread over a range of cure temperature.

12. The method of claim 9, wherein the forming of the one or more additional slabs includes forming the one or more additional slabs such that the second layers of the additional slabs are spread over a range of ratio of cure material.

13. A method of evaluating material properties comprises:
forming plural test slabs of organic matrix material, wherein the test slabs includes first layers of curable organic matrix material in contact with respective second layers of curable organic matrix material, wherein the layers each of the test slabs have at least one of different composition or different cure characteristics, and wherein the first layers of the test slabs have at least one of different composition or different cure characteristics from each other; and
comparing curvatures of the test slabs to determine material characteristics of the test slabs.

14. The method of claim 13, wherein the forming includes forming the plural test slabs of organic matrix material such that the second layers of the test slabs have substantially the same composition and substantially the same cure characteristics.

15. The method of claim 13, wherein the forming includes forming the plural test slabs of organic matrix material such that the first layers of the test slabs cover a range of composition.

16. The method of claim 14, wherein the forming includes forming the plural test slabs of organic matrix material such that the range of composition includes a range of particle loading.

17. The method of claim 13, wherein the forming includes forming the plural test slabs of organic matrix material such that the first layers of the test slabs cover a range of cure characteristics.

18. The method of claim 13, wherein the forming includes forming the plural test slabs of organic matrix material such that the comparing curvatures includes measuring curvatures of the test slabs.

19. The method of claim 13, wherein the forming includes forming the plural test slabs of organic matrix material such that the first layers of the test slabs cover a range of at least one of different composition or different cure characteristics that includes both a linear change of materials characteristics and a nonlinear change of material characteristics.

20. The method of claim 3,
further comprising examining curvatures of the one or more additional slabs; and
wherein the determining includes determining the material characteristic of the organic matrix material from both the curvature of the test slab and the curvatures of the one or more additional slabs.

* * * * *